US 6,570,016 B1

(12) United States Patent
Astleford et al.

(10) Patent No.: US 6,570,016 B1
(45) Date of Patent: May 27, 2003

(54) PROCESS FOR PREPARING A 10,11-METHANODIBENZOSUBERANE DERIVATIVE

(75) Inventors: Bret Anthony Astleford, Martinsville, IN (US); Charles Jackson Barnett, Indianapolis, IN (US); Michael Edward Kobierski, Greenwood, IN (US); Thomas Michael Wilson, Speedway, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/979,598

(22) PCT Filed: May 30, 2000

(86) PCT No.: PCT/US00/11863

§ 371 (c)(1),
(2), (4) Date: Nov. 14, 2001

(87) PCT Pub. No.: WO00/75132

PCT Pub. Date: Dec. 14, 2000

Related U.S. Application Data

(60) Provisional application No. 60/137,284, filed on Jun. 3, 1999.

(51) Int. Cl.$^7$ .................... C07D 295/073; C07D 401/12
(52) U.S. Cl. ........................................ 544/381; 544/363
(58) Field of Search ................................. 544/381, 363

(56) References Cited

U.S. PATENT DOCUMENTS

| 5,654,304 A | 8/1997 | Pfister et al. |
| 5,889,007 A | 3/1999 | Pfister et al. |

FOREIGN PATENT DOCUMENTS

| WO | 2000/75121 | * 12/2000 |

* cited by examiner

*Primary Examiner*—Emily Bernhardt
(74) *Attorney, Agent, or Firm*—Elizabeth A. McGraw; Francis O. Ginah

(57) ABSTRACT

This invention provides a process to prepare (2R)-anti-5-{3-[4-(10,11-difluoromethanodibenzosuber-5-yl)piperazin-1-yl]-2-hydroxypropoxy}quinoline.

8 Claims, No Drawings

PROCESS FOR PREPARING A 10, 11-METHANODIBENZOSUBERANE DERIVATIVE

This application is a 371 of PCT/US00/11863, filed May 30, 2000 which claims the benefit of U.S. Provisional Application No. 60/137,284, filed on Jun. 3, 1999, said application of which is entirely incorporated herein by reference.

This invention relates to the art of synthetic organic chemistry. Specifically, the invention is a process to prepare (2R)-anti-5-{3-[4-(10,11-difluoromethanodibenzosuber-5-yl)piperazin-1-yl]-2-hydroxypropoxy}quinoline trihydrochloride salt of formula I:

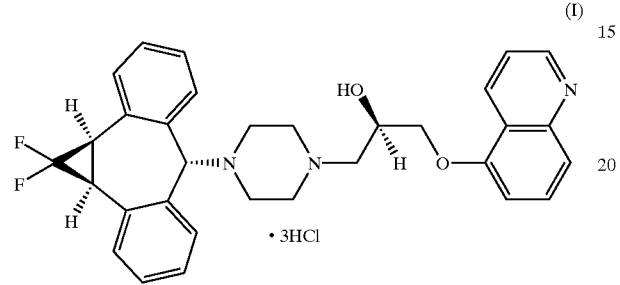

(I)

Among the problems in cancer chemotherapy is the development of resistance to treatment regimens. Tumors that respond well to a particular drug or drugs initially often develop a tolerance to the drug(s).

This disease state, called multi-drug resistance, is discussed in greater detail in Kuzmich and Tew, "Detoxification. Mechanisms and Tumor Cell Resistance to Anticancer Drugs," particularly section VII "The Multidrug-Resistant Phenotype (MDR)," *Medical Research Reviews*, Vol. 11, No. 2, 185–217, particularly 208–213 (1991); and in Georges, Sharom and Ling, "Multidrug Resistance and Chemosensitization: Therapeutic Implications for Cancer Chemotherapy," *Advances in Pharmacology*, Vol. 21, 185–220 (1990).

U.S. Pat. Nos. 5,643,909 and 5,654,304, incorporated herein by reference, disclose a series of 10,11-methanobenzosuberane derivatives useful in enhancing the efficacy of existing cancer chemotherapeutics and for treating multidrug resistance. (2R)-anti-5-{3-[4-(10,11-difluoromethanodibenzosuber-5-yl)piperazin-1-yl]-2-hydroxypropoxy}quinoline trihydrochloride disclosed therein, is currently under development as a pharmaceutical agent. The present invention involves an improved process to prepare (2R)-anti-5-{3-[4-(10,11-difluoromethanodibenzosuber-5-yl)piperazin-1-yl]-2-hydroxypropoxy}quinoline trihydrochloride (compound of formula I), wherein the chemistry is more efficient and adaptable to large scale processing in anticipation of development needs.

The art disclosed in U.S. Pat. No. 5,776,939, and U.S. Pat. No. 5,643,909 both incorporated herein by reference, and PCT Patent Applications (Publication numbers WO 94/24107 and 98/22112) teach the use of 1-formylpiperazine to introduce the piperazine group of the compound of formula II

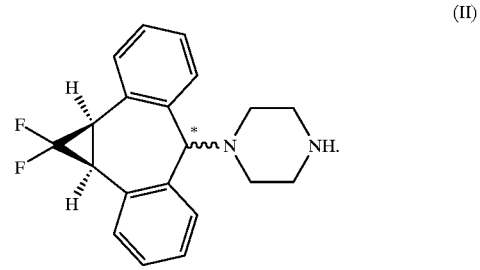

(II)

Compound II is a mixture of syn isomer (III)

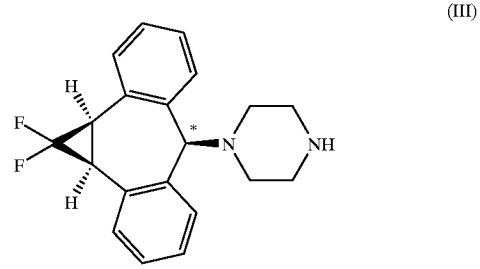

(III)

and anti isomer (IV)

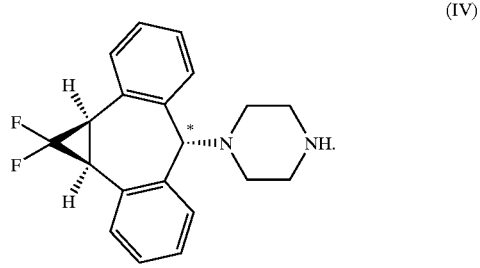

(IV)

The process as disclosed in U.S. Pat. Nos. 5,643,909 and 5,654,304 (represented by scheme A, below) involves (a) chromatographic separation(s) of the formyl piperazine compound; and (b) deformylation of the formyl piperazine compound to provide compound IV.

Scheme A

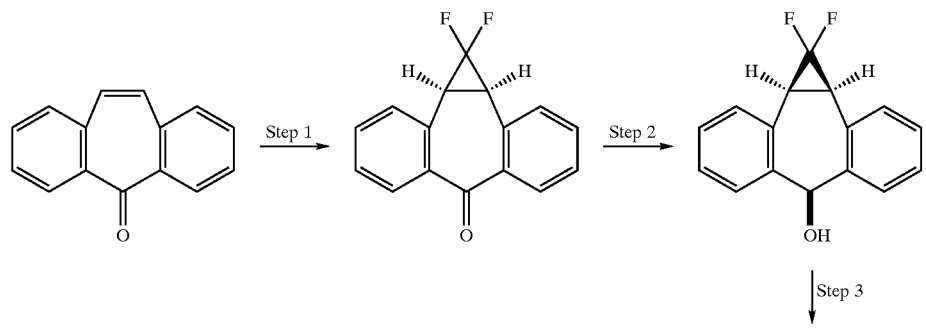

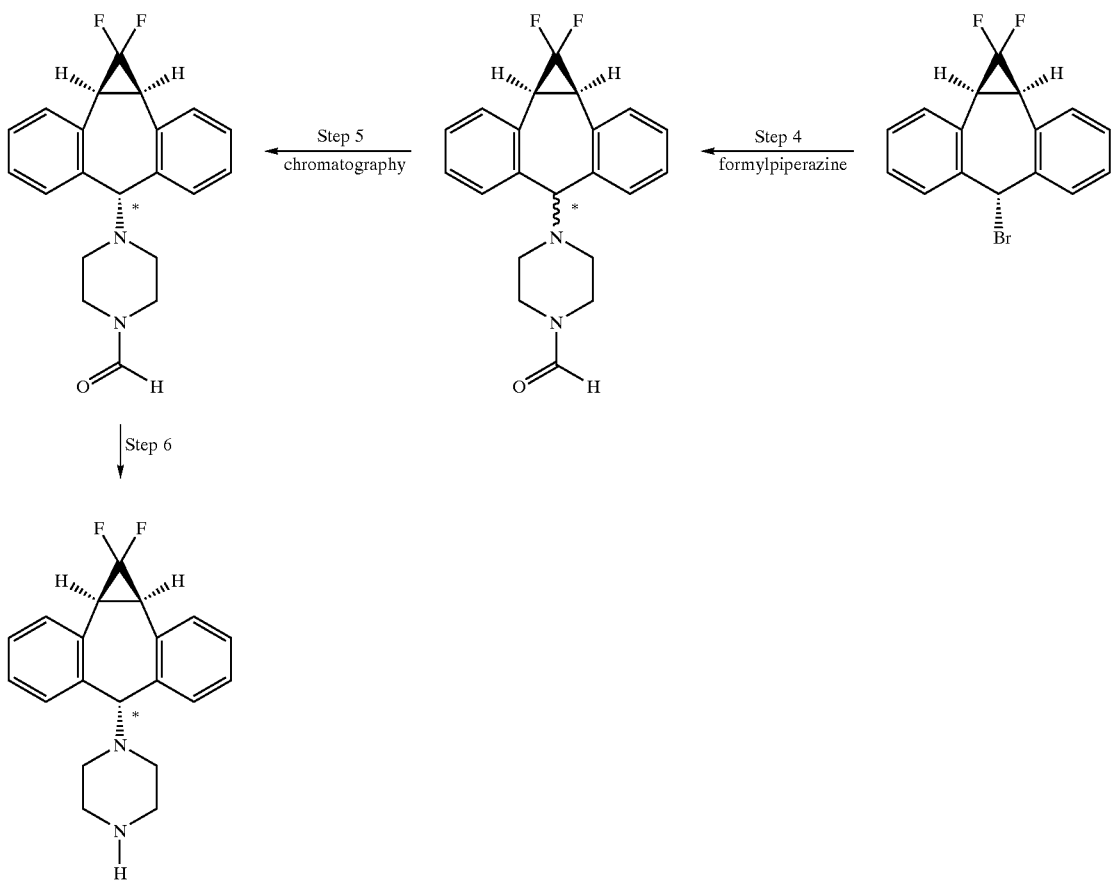

The process of the present invention uses piperazine to react with the (1aα,6α,10bα)-6-halo-1,1-difluoro-1,1a,6,10b-tetrahydrodibenzo[a,e]cyclopropa[c]-cycloheptene compound or derivative, instead of formylpiperazine.

The process of the present invention is advantageous because piperazine is readily available in commercial quantities whereas 1-formylpiperazine, which was utilized in the process disclosed in U.S. Pat. No. 5,643,909 is often not readily available in commercial quantities. Additionally piperazine enjoys a significant cost advantage over 1-formylpiperazine.

The use of piperazine instead of 1-formylpiperazine is a significant advancement over the prior art because it obviates the need to deformylate or hydrolyze off the formyl group (step 6, scheme A), thereby providing fewer operational steps. U.S. Pat. No. 5,643,909 teaches the separation of the 1-formylpiperazine compounds by chromatography or repeated crystallization. The present invention obviates the need for chromatographic separations of the formylpiperazine diastereomeric addition compounds (see step 4, scheme A)

The present invention provides a process for preparing a compound of the formula (IVa):

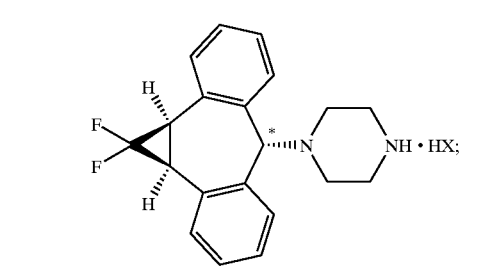
(IVa)

wherein HX is an acid, comprising the steps of:

(a) dissolving a compound of formula (II)

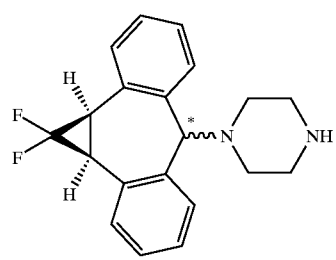
(II)

in acetonitrile to form a solution;

(b) crystallizing a syn stereoisomer compound of formula (III)

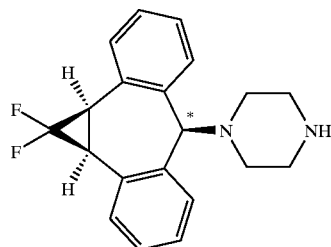

from the solution of (II);

(c) removing the acetonitrile from the filtrate to provide a mixture enriched in an anti stereoisomer compound of formula (IV)

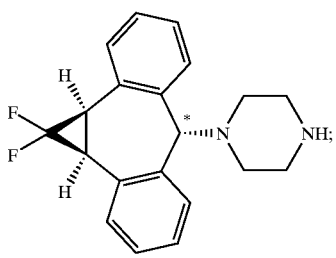

(d) adding an acid, and a solvent selected from the group consisting of methylene chloride, ethanol and ethyl acetate to said enriched mixture; and (e) crystallizing the anti-stereoisomer compound of formula (IVa).

The present invention also provides a process for preparing a compound of formula (IVa),

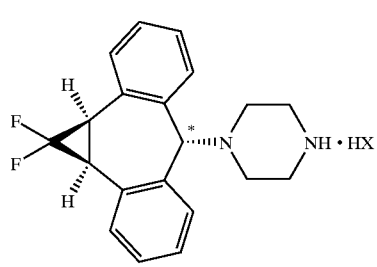

comprising the steps of:

(a) converting 10,11-dibenzosuberenone (i),

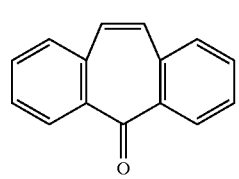

to the alcohol (ii),

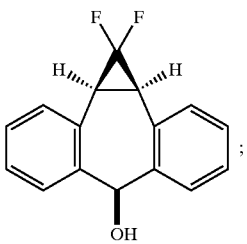

(b) reacting alcohol (ii) in one operational step with a halogenating agent to form (1aα,6α,10bα)-6-halo-1,1-difluoro-1,1a,6,10b-tetrahydrodibenzo[a,e]-cyclopropa[c]cycloheptene (iii);

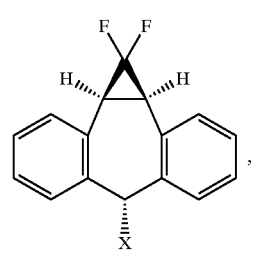

where X is I, Br, or Cl;

(c) reacting (1aα,6α,10bα)-6-halo-1,1-difluoro-1,1a,6,10b-tetrahydrodibenzo[a,e]cyclopropa[c]-cycloheptene (iii) with piperazine in a solvent to form the mixture of syn (III)

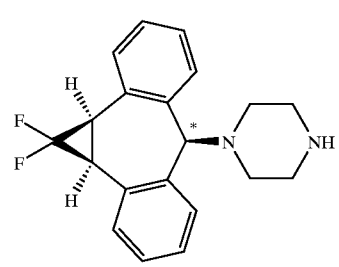

and anti (IV)

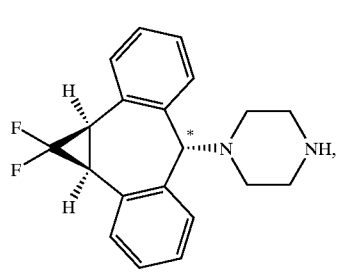

piperazine compounds, and (d) separating the compound of formula III from the compound of formula IV by the method of the invention.

The present invention also provides a process for preparing a compound of formula (I) from the anti stereoisomer IVa, according to the invention, comprising the steps of:

(a) reacting the anti-stereoisomer (IVa) as the free base, with (R)-1-(5-quinolinyloxy)-2,3-epoxypropane to provide compound of formula (V);

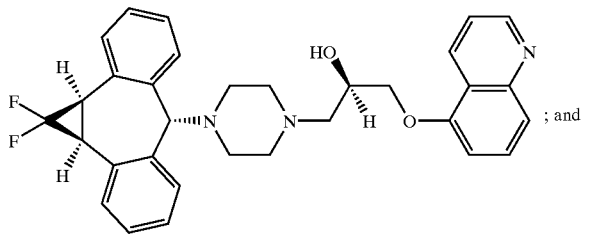

(V)

; and (b) optionally reacting hydrogen chloride with compound (V) to form a compound of formula (I):

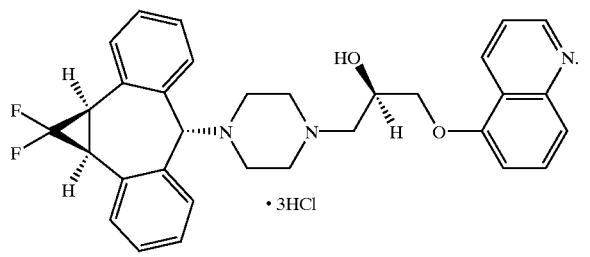

(I)

· 3HCl

The present invention further provides a process for preparing the syn isomer compound (III) and pharmaceutically acceptable salts thereof, by the method of the invention.

The terms and abbreviations used herein have their normal meanings unless otherwise designated. For example "° C." refers to degrees Celsius; "N" refers to normal or normality; "mmol" refers to millimole or millimoles; "g" refers to gram or grams; "d" refers to density, "min." refers to minutes, "mL" means milliliter or milliliters; "M" refers to molar or molarity; "HPLC" refers to high performance liquid chromatography; "mm" refers to millimeters; "cm" refers to centimeters; "nm" refers to nanometers; and "rt" refers to retention time. The term "halo" refers to fluoro, bromo, chloro and iodo.

As used herein the term "halogenating agent" refers to halogenic acids or other acidic groups capable of converting alcohols to halides. Illustrative halogenating agents include hydrogen bromide, hydrogen chloride, hydrogen iodide, thionyl chloride, oxalyl chloride, phosphorus trichloride or pentachloride, and the like.

As used herein, the term "pharmaceutically acceptable salt" refers to all non-toxic organic or inorganic acid addition salts. Illustrative inorganic acids or "acidic groups" which form salts include hydrochloric, hydrobromic, sulfuric, phosphoric acid and acid metal salts such as sodium monohydrogen orthophosphate, and potassium hydrogen sulfate. Illustrative acids or "acidic groups" which form suitable salts include the mono-, di- and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxy-benzoic, and sulfonic acids such as p-toluenesulfonic acid, methanesulfonic acid, camphorsulfonic acid, and 2-hydroxyethane sulfonic acid. Preferred acids include those selected from the group comprising of hydrobromic acid, hydrochloric acid, camphorsulfonic acid, p-toluenesulfonic acid, and sulfuric acid. A particularly preferred acidic group is hydrochloric acid. Acid addition salts formed from these acids can exist in either hydrated or substantially anhydrous form, all of which are within the scope of this invention.

The terms "HX," "acidic group," and "acid" are synonymous as used herein.

The compounds of formula II may be prepared according to the following steps illustrated in Scheme B, starting from 5H-dibenzo[a,d]cyclohepten-5-one (dibenzosuberenone), which is commercially available, e.g., from Aldrich Chemical Company, Milwaukee, Wis. Other reactants are likewise commercially available or may be readily prepared by those skilled in the art. A particularly preferred embodiment of this invention provides a procedure that combines steps 1 and 2 (see Scheme B below) in one operational step.

Scheme B

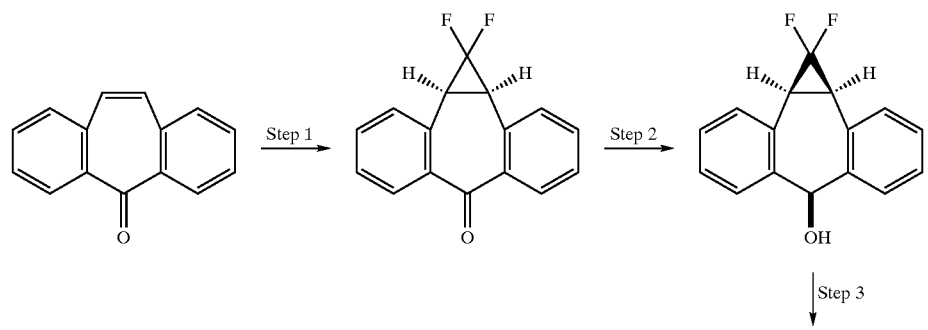

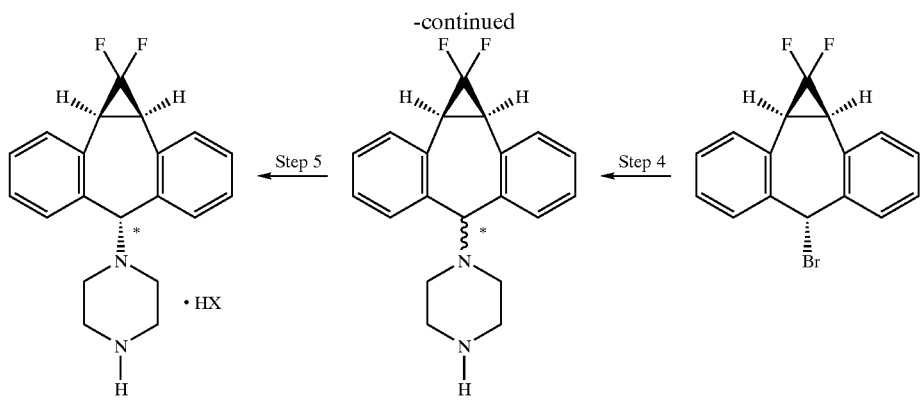

Step 1: A solution of an alkali halodifluoroacetate such as sodium chlorodifluoroacetate in a solvent (for example, glyme, diglyme) is added over a period of 4 to 8 hours (preferably 6 hours) to a solution of dibenzosuberenone (for example in diglyme) with stirring and under nitrogen, maintaining the reaction temperature at 160°–165° C. Other reaction temperatures may be employed depending upon the reactants used, as described in Ciganek et al., "Imine Analogues of Tricyclic Antidepressants," *J. Med. Chem.*, 1981, 24,336–41; or in Coyne and Cusic, "Aminoalkyldibenzo[a,e]cyclopropa[c]cycloheptene Derivatives. A Series of Potent Antidepressants," *J. Med. Chem.*, 1974, Vol. 17, No. 1, 72–75. The reaction mixture is brought to room temperature, then poured into water and extracted (e.g., with diethylether or pentane). The 1,1-difluoro-1a,10b-dihydrodibenzo[a,e]cyclopropa[c]cyclohepten-6(1H)-one is isolated and purified by conventional means, for example, the organic phase is washed with water, dried (e.g., over $Na_2SO_4$), evaporated, and the residue is recrystallized (e.g., from ethanol, and optionally recrystallized again, e.g., from acetone/hexane).

Step 2: A solution of the 1,1-difluoro-1a,10b-dihydrodibenzo[a,e]cyclopropa[c]cyclohepten-6(1H)-one in a solvent (e.g., THF/methanol) is cooled typically to between 0° C. and 25° C., and a reducing agent (e.g., lithium borohydride or sodium borohydride) is added in portions. The reaction mixture is allowed to come to room temperature and stirred for 1 to 5 hours preferably 2 hours, then poured into water. The product is isolated (e.g., by filtration) and purified by conventional means (e.g., washed with water and dried) to give the corresponding (1aα,6β,10bα)-1,1-difluoro-1,1a,6,10b-tetrahydrodibenzo[a,e]cyclopropa[c]-cyclohepten-6-ol (ii).

Preferably steps-1 and 2 may be accomplished in one processing step by heating a solution of dibenzosuberenone in triethylene glycol dimethyl ether to between 180° C. and 210° C., followed by slow addition of a solution of chlorodifluoroacetic acid, lithium salt in ethylene glycol dimethyl ether. The ethylene glycol dimethyl ether is distilled from the reaction as the salt addition proceeded. Gas chromatographic analysis of an aliquot is utilized to indicate complete or near complete consumption of the 5H-dibenzo[a,d]cyclohepten-5-one. The reaction is cooled to ambient temperature and then combined with a mixture of ethyl acetate and diatomaceous earth. The solids are removed by filtration and washed with ethyl acetate. The washes and filtrate are combined and the ethyl acetate is removed by concentration under vacuum. The concentrate is cooled, followed by addition of sodium borohydride solution sufficient to effect complete or near complete reduction. After stirring for 1–5 h, preferably 2–4 hours, the reaction is quenched by careful addition of a methanolic HCl solution. The suspension is stirred for 30 minutes and the crude product is collected by filtration, washed with 1:1 methanol-water and dried to a dark brown solid. The crude product is slurried in methylene chloride, filtered and dried to afford (1aα,6β,10bα)-1,1-difluoro-1,1a,6,10b-tetrahydrodibenzo-[a,e]cyclopropa[c]cyclohepten-6-ol (ii).

Step 3: A solution of the (1aα,6β,10bα)-1,1-difluoro-1,1a,6,10b-tetrahydrodibenzo[a,e]cyclopropa[c]-cyclohepten-6-ol in a suitable solvent (e.g., dichloromethane) is cooled (e.g., in an ice bath) followed by addition of a halogenating agent. Preferred halogenating agents are hydrogen bromide, hydrogen chloride, hydrogen iodide, thionyl chloride, oxalyl chloride, phosphorus trichloride or pentachloride, and the like. Most preferred are hydrogen chloride and hydrogen bromide. The reaction is maintained at a temperature of between 40° to 70° C., preferably 50° C., for 2 to 5 hours (preferably 4 hours). The reaction mixture is evaporated to dryness, affording a mixture of (1aα,6α,10bα)-6-halo-1,1-difluoro-1,1,a,6,10b-tetrahydrodibenzo[a,e]-cyclopropa[c]cycloheptene and the corresponding syn isomer (1aα,6β,10bα)-6-halo-1,1-difluoro-1,1,a,6,10b-tetrahydrodibenzo[a,e]cyclopropa[c]cycloheptene. In the case of the bromo derivative the bromination reaction provides the anti-stereoisomer ((1aα,6α,10bα)-6-bromo-1,1-difluoro-1,1,a,6,10b-tetrahydrodibenzo[a,e]cyclopropa[c]-cycloheptene) (iii) exclusively. Preparation of the (1aα,6α,10bα)-6-bromo-1,1-difluoro-1,1,a,6,10b-tetrahydrodibenzo[a,e]cyclopropa[c]cycloheptene derivative (iii) is preferably accomplished by reacting the (1aα,6β,10bα)-1,1-difluoro-1,1a,6,10b-tetrahydrodibenzo[a,e]cyclopropa[c]cyclohepten-6-ol (ii) with hydrogen bromide.

Combined steps 4 and 5: The (1aα,6α,10bα)-6-halo-1,1-difluoro-1,1,a,6,10b-tetrahydrodibenzo-[a,e]cyclopropa[c]cycloheptene product of step 3, is with or without further purification, dissolved in acetonitrile. Piperazine is introduced by nucleophilic displacement of the halide e.g., by adding piperazine with stirring, preferably under dry nitrogen. The reaction temperature is maintained between 50° C. to 100° C., preferably between 70° C. to 90° C., for 1 to 6 hours, preferably 2 hours. The mixture of syn and anti-stereoisomers (II) is preferably separated by crystallization of the syn stereoisomer from the acetonitrile reaction mixture. This is followed by removal of the remaining acetonitrile and replacement with hydrogen bromide or other suitable acid and a solvent selected from methylene chloride, ethanol and ethyl acetate. The purified (1aα,6α,10bα)-1-(1,1-difluoro-1,1a,6,10b-tetrahydrodibenzo[a,e]cyclopropa[c]-cyclohepten-6-yl)-piperazine, acid salt compound (IVa) is afforded after crystallization.

The isolated syn isomer product III from above may be dried, used directly or optionally further purified by methods known in the arts, e.g., crystallization, chromatography. The syn isomer compound of formula (III) may optionally be acidified to form a pharmaceutically acceptable acid salt.

The acid salt-compound (IVa) may be converted to the compounds of formula I as illustrated in scheme C below:

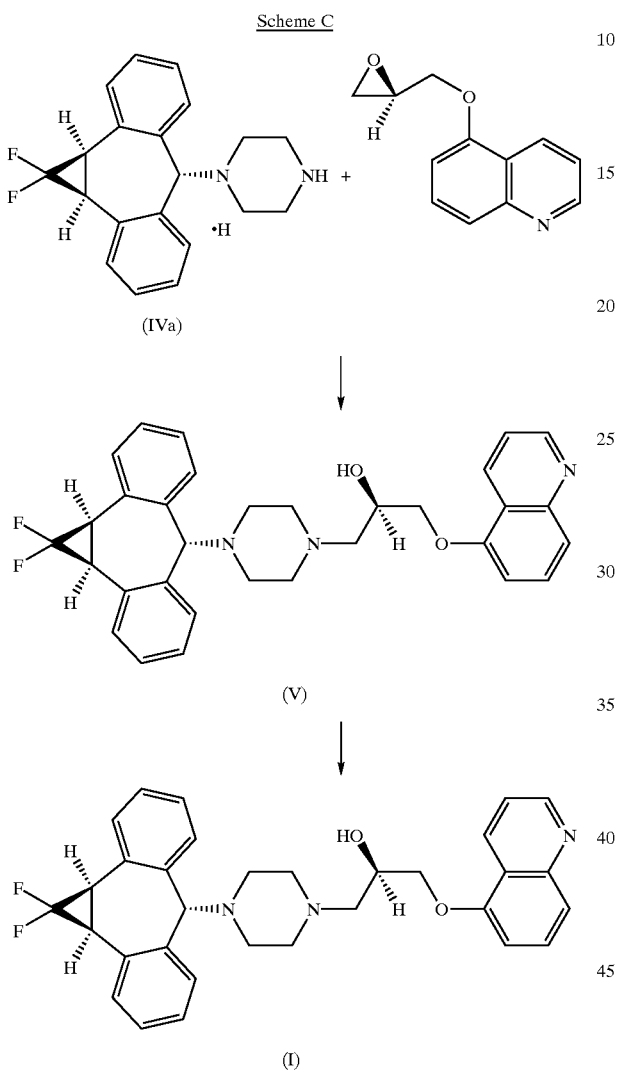

The syn isomer compound of formula (III) isolated as described supra, can be acidified to form the acid salt compound of formula (IIIa):

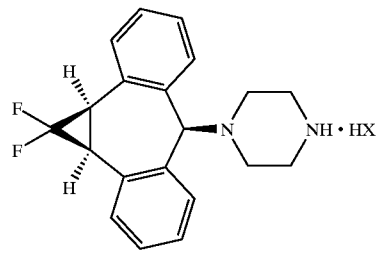

Optionally, the syn isomer compound of formula (III) can be utilized to produce the corresponding syn-5-{3-[4-(10,11-difluoromethano-dibenzosuber-5-yl)piperazin-1-yl]-2-hydroxypropoxy}quinoline trihydrochloride compound of formula (XII)

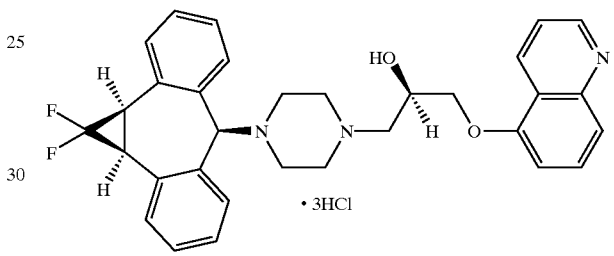

essentially as shown above for the free base of the anti isomer (IVa).

EXAMPLES

The following examples and preparations are illustrative only and are not intended to limit the scope of the invention in any way.

Preparation 1

R-1-(5-Quinolinyloxy)-2,3-epoxypropane

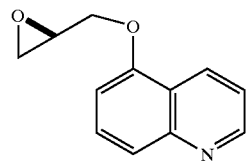

(1aα,6α,10bα)-1-(1,1-difluoro-1,1a,6,10b-tetrahydrodibenzo[a,e]cyclopropa[c]cyclohepten-6-yl)-piperazine, acid salt compound (IVa) after conversion to the free base (IV) by neutralization, is reacted with a solution of the epoxide, (R)-1-(5-quinolinyloxy)2,3-epoxypropane (compound of formula 8), in a solvent such as ethanol or isopropanol, to produce-(2R)-anti-5-{3-[4-(10,11-difluoromethano-dibenzosuber-5-yl)piperazin-1-yl]-2-hydroxypropoxy}quinoline (V). Acid salts of (V) may be prepared by methods known to those skilled in the art. The preferred trihydrochloride salt, anti-5-{3-[4-(10,11-difluoromethano-dibenzosuber-5-yl)piperazin-1-yl]-2-hydroxypropoxy}quinoline trihydrochloride (I), may be prepared by addition of hydrogen chloride in diethyl ether (e.g., 3 molar equivalents to form the trihydrochloride (salt) at 0–15° C. followed by, for example, recrystallization from ethanol.

A mixture of 5-hydroxyquinoline (5.60 g, 38.6 mmol), R-glycidyl nosylate (10.0 g, 38.6 mmol), powdered potassium carbonate (11.7 g, 84.9 mmol), and N,N-dimethylformamide (100 mL) was stirred at ambient temperature until HPLC analysis (40% acetonitrile/60% of a 0.5% aqueous ammonium acetate solution, 1 mL/min, wavelength=230 nm, Zorbax RX-C8 25 cm×4.6 mm column) indicated complete disappearance of glycidyl nosylate (approximately 6 hours). The reaction mixture was filtered through paper and the filter cake was washed with 200 mL of a 3:1 mixture of MTBE and methylene chloride. The filtrate was washed with 200 mL of water and the aqueous layer was extracted four times with 100 mL of 3:1

MTBE/methylene chloride. The combined organic layers were dried over 30 grams of magnesium sulfate and the dried solution was then stirred with 50 grams of basic alumina for 30 minutes. The alumina was removed by filtration and the filter cake was washed with 200 mL of 3:1 MTBE/methylene chloride. The filtrate was concentrated to a volume of 100 mL, 300 mL of MTBE were added, and the solution was again concentrated to 80 mL. After heating to 50° C., the solution was treated with 160 mL of heptane dropwise over 15 minutes, allowed to cool to 40° C., and seeded, causing the formation of a crystalline precipitate. The mixture was stirred for two hours at ambient temperature and then at 0–5° C. for an additional 2 hours. The crystals were filtered, washed with cold heptane, and dried to provide 5.68 g (73.2%) of (2R)-1-(5-quinolinyloxy)-2,3-epoxypropane as white needles.

mp 79–81° C.;

[α]$^{25}_D$ -36.4° (c 2.1, EtOH);

$^1$H NMR (500 MHz, CDCl$_3$)δ 2.83 (dd, J=4.8, 2.7 Hz, 1H), 2.97 (m, 1H), 3.48 (m, 1H), 4.10 (dd, J=11.0, 6.0 Hz, 1H), 4.43 (dd, J=11.0, 2.7 Hz, 1H), 6.85 (d, J=7.8 Hz, 1H), 7.38 (dd, J=8.5 Hz, 4.1 Hz, 1H), 7.59 (m, 1H), 7.71 (d, J=8.5 Hz, 1H), 8.61 (m, 1H), 8.90 (m, 1H).

Example 1

(2R)-Anti-1-[4-(10,11-difluoromethano-10,11-dihydro-5H-dibenzo[a,d]cyclohepten-5-yl)-piperazin-1-yl]-3-qunolin-5-yloxy)-propan-2-ol Trihydrochloride

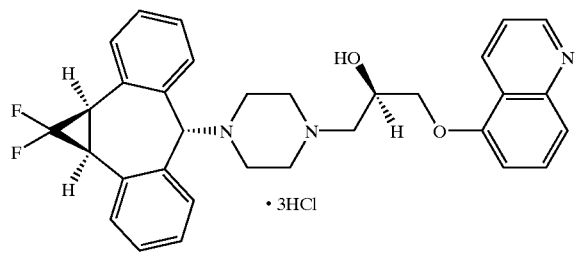

Preparation of the above compound is exemplified in the following preparative steps.

Step 1

1,1-Difluoro-1a,10b-dihydrodibenzo[a,e]cyclopropa[c]-cyclohepten-6 (1H)-one

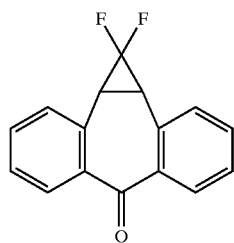

A solution of sodium chlorodifluoroacetate (350 g) in diglyme (1400 mL) was added dropwise over 4 to 8 hours, preferably over 6 hours, to a solution of 5H-dibenzo[a,d]cyclo-hepten-5-one (25 g) in diglyme (500 mL), with stirring, and under nitrogen, maintaining the reaction temperature at 160°–165° C. The cooled reaction mixture was poured into water (1.8 L) and extracted with ether (1.8 L). The organic phase was washed with water, dried over sodium sulfate (Na$_2$SO$_4$), and evaporated. The residue was recrystallized from ethanol, then from acetone/hexane to give 14 g of 1,1-difluoro-1a,10b-dihydrodibenzo[a,e]cyclopropa[c]-cyclohepten-6(1H)-one.

mp 149.6° C.

Flash chromatography of the combined mother liquors on silica gel, eluting with 20% acetone/hexane, gave an additional 6.5 g of the target compound.

Step 2

(1aα,6β,10bα)-1,1-Difluoro-1,1a,6,10b-tetrahydrodibenzo[a,e]cyclopropa[c]cyclohepten-6-ol

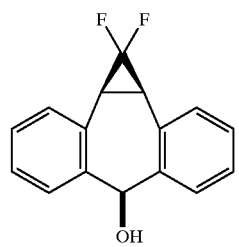

A solution of 1,1-difluoro-1a,10b-dihydro-dibenzo[a,e]cyclopropa[c]cyclohepten-6(1H)-one (20.4 g) in tetrahydrofuran/methanol (1:2, 900 mL) was cooled in an ice bath. Sodium borohydride (12 g) was added in portions. The cooling bath was removed and the reaction mixture was stirred at ambient temperature for 2 hours, then poured into water. The product was filtered off, washed with water, and dried to give 20 g of (1aα,6β,10bα)-1,1-difluoro-1,1a,6,10b-tetrahydrodibenzo[a,e]cyclopropa[c]cyclohepten-6-ol (ii).

mp 230.1°–230.6° C.

Step 2A

Combined Steps 1 and 2 Procedure (1aα,6β,10bα)-1,1-Difluoro-1,1a,6,10b-tetrahydrodibenzo[a,e]cyclopropa[c]cyclohepten-6-ol

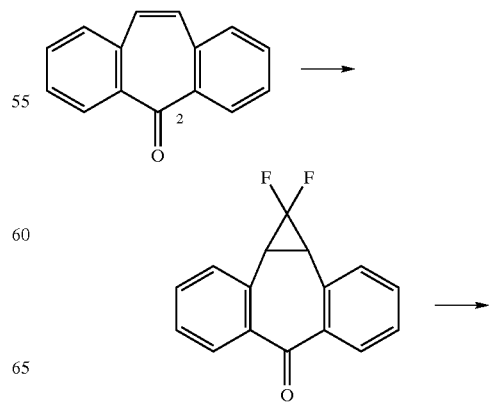

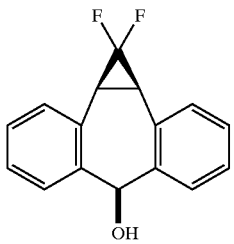

To a solution of 103.1 g (0.500 mol) of 5H-dibenzo[a,d] cyclohepten-5-one (2) in 515 mL of triethylene glycol dimethyl ether heated to between 180° C. and 210° C. was added over 7 hours, 293.3 g (2.15 mol) of chlorodifluoroacetic acid lithium salt (as a 53% by weight solution in ethylene glycol dimethyl ether). The ethylene glycol dimethyl ether was allowed to distill from the reaction as the salt addition proceeded. The GC analysis of an aliquot indicated that all of the 5H-dibenzo[a,d]cyclohepten-5-one had been consumed. The reaction was cooled to ambient temperature and then combined with 400 mL of ethyl acetate and 75 g of diatomaceous earth. The solids were removed by filtration and washed with 300 mL of ethyl acetate. The washes and filtrate were combined and the ethyl acetate was removed by concentration under vacuum leaving 635 g of dark liquid. The dark liquid was cooled to 18° C. and to this was added, over 15 minutes, 6.62 g (0.175 mol) of sodium borohydride (as a 12% by wt solution in 14 M NaOH). After stirring for 2 h the reaction was quenched by careful addition of 900 mL of a 1:3.5:4.5 solution of conc. HCl-methanol-water. The suspension was stirred for 30 min and the crude product was collected by filtration, washed with 600 mL of 1:1 methanol-water and dried to 126.4 g of dark brown solid. The crude product was slurried in 600 mL of methylene chloride, filtered, washed twice with 150 mL portions of methylene chloride, and dried to 91.6 g (71%) of (1aα,6β,10bα)-1,1-difluoro-1,1a,6,10b-tetrahydrodibenzo[a,e]cyclopropa[c]-cyclohepten-6-ol. Gas Chromatography (GC) Conditions; Column: JW Scientific DB-1, Initial Temperature 150° C. for 5 min, 10° C./min ramp, Final temp 250° C. for 5 min. $t_R$: intermediate, 11.5 min; reaction product (alcohol), 11.9 min; starting material, 12.3 minutes.

Step 3

Preparation of (1aα,6α,10b)-6-bromo-1,1-difluoro-1,1a,6,10b-tetrahydrodibenzo[a,e]cyclopropa-[c] cycloheptene

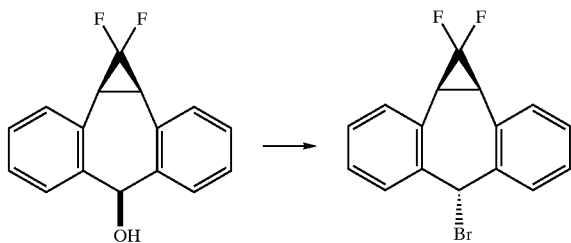

A slurry of (1aα,6β,10bα)-1,1-difluoro-1,1a,6,10b-tetrahydrodibenzo[a,e]cyclopropa[c]-cyclohepten-6-ol (3.0 g, 11.6 mmol, 1.0 equiv) in heptane (24 mL) was treated with 48% HBr (1.58 mL, 14.0 mmol, 1.2 equiv) and the reaction was heated at reflux with vigorous stirring for 2.5 hr. Solvent was then removed by atmospheric distillation (bp 95–98° C.) until approximately 9 mL of distillate was collected. The reaction was cooled and treated with EtOAc (15 mL), $Na_2SO_4$ and activated charcoal. The mixture was stirred at RT for 15 min and filtered through hyflo. The filter cake was washed with 50:50 EtOAc:heptane and the filtrate was concentrated in vacuo to provide the title product as a crystalline solid.

mp 119° C. (3.46 g corr., 93%);

$^1$H NMR (500 MHz $CDCl_3$) δ 7.20–7.41 (8H, m), 5.81 (1H, s), 3.41 (2H, d, J 12.5 Hz);

$^{13}$CNMR (126 MHz $CDCl_3$) δ 141.3, 141.2, 133.5, 130.1, 129.8, 128.3, 128.2, 112.9, 110.6, 110.5, 108.3, 53.6, 30.2, 30.1, 30.0.

Anal. Calcd. For $C_{16}H_{11}BrF_2$: C, 59.84; H, 3.45. Found: C, 60.13; H, 3.50.

Step 3A

Preparation of (1aα,6α,10bα)-6-Bromo-1-difluoro-1,1a,6,10b-tetrahydrodibenzo[a,e]cyclopropa[c] cycloheptene

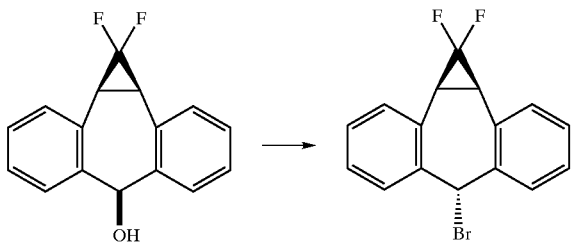

To a stirred suspension of (1aα,6β,10bα)-1,1-difluoro-1,1a,6,10b-tetrahydrodibenzo[a,e]cyclopropa[c]-cyclohepten-6-ol, (18.4 g, 71.2 mmol) in 151 mL of methylene chloride which had been cooled to 10–17° C. was added phosphorous tribromide (9.6 g, 35.6 mmol) dropwise over 15 minutes. The cooling bath was removed and the reaction was stirred for 2 hours at ambient temperature. Analysis by gas chromatography indicated complete consumption of starting material. Cold water (92 mL) and activated carbon (1.84 g) were added and the resulting mixture was stirred for 30 minutes. The activated carbon was removed by filtration through Hyflo brand filter aid and the two phases were separated. The organic phase was washed with water (184 mL×2), brine (184 ml), dried over magnesium sulfate and concentrated to dryness under vacuum, affording 21.7 g (94.8%) of (1aα,6α,10bα)-6-bromo-1,1-difluoro-1,1a,6,10b-tetrahydrodibenzo[a,e]cyclopropa[c]cycloheptene.

$^1$H NMR ($CDCl_3$, 300 MHz) δ 3.36 (s, 1H), 3.40 (s, 1H), 5.77 (s, 1H), 7.16–7.38 (m, 8H).

Steps 4 and 5

(1aα,6α,10bα)-1-(1,1-Difluoro-1,1a,6,10b-tetrahydrodibenzo[a,e]cyclopropa[c]cyclohepten-6-yl)-piperazine, Hydrobromide Salt

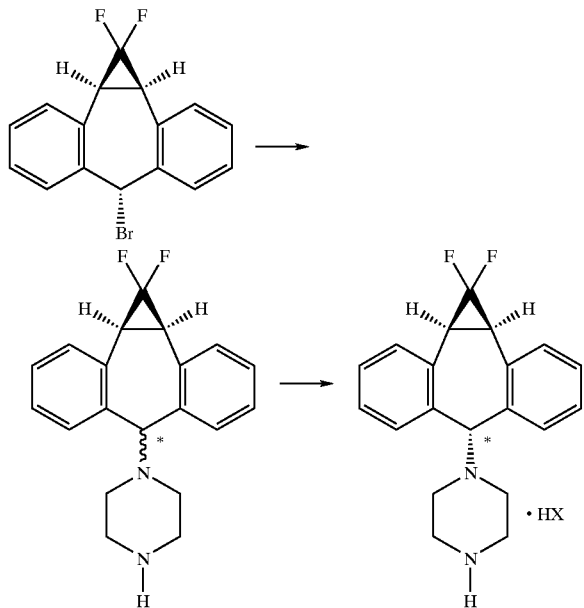

To a solution of 237.5 g (0.739 mol) of (1aα,6α,10bα)-6-bromo-1,1-difluoro-1,1a,6,10b-tetrahydrodibenzo[a,e]-cyclopropa[c]cycloheptene in 3.56 L of acetonitrile was added 207.7 g (2.41 mol) of piperazine and the mixture was heated to reflux for 2 hours, at which time analysis by gas chromatography showed complete consumption of (1aα,6α,10bα)-6-bromo-1,1-difluoro-1,1a,6,10b-tetrahydrodibenzo[a,e]cyclopropa[c]cycloheptene (iii) and formation of a mixture of syn and anti piperazine compounds (III and IV) in an anti-syn ratio of 55:45. The reaction was cooled to about 7° C. and stirred for 30 minutes at that temperature. The reaction mixture was filtered to remove the precipitated syn-isomer (III) and the filter cake was washed with 250 mL of acetonitrile. The combined filtrate and wash were concentrated under vacuum to 262.4 grams of a foam which was dissolved in 450 mL of acetonitrile with heating. The solution was cooled to about 12° C. in an ice bath and stirred for 1 hour at that temperature. The precipitated syn-piperazine compound of formula (III) was filtered and washed with 125 ml of acetonitrile. The combined filtrate and wash were concentrated under vacuum to 194.1 g and dissolved in 1.19 L of ethyl acetate. The organic solution was washed sequentially with 500 mL portions of 1N sodium hydroxide, water, and saturated sodium chloride. The ethyl acetate solution was dried over sodium sulfate and concentrated to give 137.0 grams of residue which was dissolved in 1.37 L of methylene chloride and seeded with (1aα,6α,10bα)-1-(1,1-difluoro-1,1a,6,10b-tetrahydrodibenzo[a,e]cyclopropa[c]-cyclohepten-6-yl)-piperazine, hydrobromide salt, followed by the addition of 70.8 grams of 48% aqueous hydrobromic acid. The mixture was stirred for about 45 minutes, causing the anti-isomer to crystallize as its hydrobromide salt. The crystals were filtered, washed with methylene chloride, and dried to provide purified hydrobromide salt of compound (IVa), shown by HPLC to have an anti-syn ratio of 99.3:0.7. Treatment of the isolated hydrobromide salt of compound (IVa) with aqueous sodium hydroxide, extraction into methylene chloride, separation of the aqueous layer and concentration to dryness gave 80.1 grams (33.2% yield based on starting material) of (1aα,6α,10bα)-1-(1,1-difluoro-1,1a,6,10b-tetrahydrodibenzo[a,e]cyclopropa[c]-cyclohepten-6-yl)-piperazine as the free base. Acidification of a solution of the free base in 800 mL of methylene chloride by addition of 41.2 g of 48% hydrobromic acid as described above afforded 96.4 g of pure hydrobromide salt (title compound) with an anti-syn ratio of 99.8:0.2 (HPLC), mp 282–284° C. $^{1}$H NMR (DMSO-$d_6$) δ 2.41 (m, 4H), 3.11 (m, 4H), 3.48 (d, J=12.4 Hz, 2H), 4.13 (s, 1H), 7.2 (m, 8H), 8.65 (bs, 2H). $^{13}$C NMR (DMSO-$d_6$) δ 28.0, 42.9, 48.0, 75.1, 108.5, 112.9, 117.3, 127.5, 128.0, 128.6, 129.6, 132.4, 141.3. IR: (KBr) 3019, 2481, 1587, 1497, 1298 cm$^{-1}$. Anal. Calcd for $C_{20}H_{21}BrF_2N_2$: C, 58.98; H, 5.20; N, 6.88. Found: C, 58.75; H, 5.29; N, 7.05.

Step 6

Preparation of (2R)-Anti-1-[4-(10,11-difluoromethano-10,11-dihydro-5H-dibenzo[a,d]cyclohepten-5-yl)-piperazin-1-yl]-3-quinolin-5-yloxy)propan-2-ol Trihydrochloride A suspension of (1aα,6α,10bα)-1-(1,1-difluoro-1,1a,6,10b-tetrahydrodibenzo[a,e]cyclopropa[c]-cyclohepten-6-yl)-piperazine, hydrochloride compound of formula IVa (5.41 g, 14.9 mmol) and powdered sodium carbonate (3.16 g, 29.8 mmol) in 54 mL of 3A ethanol was stirred at ambient temperature for 1 hour. R-1-(5-quinolinyloxy)-2,3-epoxypropane (3.00 g, 14.9 mmol) was added in one portion and the reaction mixture was heated to 65° C. for 19 hours. HPLC analysis (Gradient system with solvent A (acetonitrile) and solvent B (0.02M sodium monophosphate buffer containing 0.1% triethylamine adjusted to pH 3.5 with phosphoric acid) as follows: 0–12 min, 30% solvent A/70% solvent B; 12–30 min, linear gradient from 30% to 55% solvent A/70% to 45% solvent B; 30–35 min, 55% solvent A/45% solvent B, 1 mL/min, 1=240 nm, Synchropak SCD-100 25 cm×4.6 mm column) indicated the total consumption of the piperazinyl compound of formula (IV). The mixture was allowed to cool to room temperature, filtered through a plug of silica gel, and eluted with an additional 90 mL of ethanol. The eluent was concentrated to a volume of approximately 60 mL and heated to 65° C. with stirring. A solution of HCl in ethanol (16.1 g at 0.135 g/g of solution, 59.6 mmol) was added dropwise over 10 minutes and the resultant product solution was seeded, causing the trihydrochloride salt to precipitate. The mixture was allowed to cool to ambient temperature and stirred slowly (less than 100 RPM) for 2 hours. The precipitate was filtered, washed with ethanol, and dried in vacuo at 50° C. to give the crude trihydrochloride salt which was further purified by recrystallization from methanol/ethyl acetate to provide 7.45 g (78.4%) of (2R)-anti-1-[4-(10,11-difluoromethano-10,11-dihydro-5H-dibenzo[a,d]cyclohepten-5-yl)-piperazin-1-yl]-3-quinolin-5-yloxy)-propan-2-ol trihydrochloride.

Step 6a

The syn isomer compound of formula (III) isolated as described supra (combined steps 4 and 5), can be utilized to produce the corresponding syn-5-{3-[4-(10,11-difluoromethano-dibenzosuber-5-yl)piperazin-1-yl]-2-hydroxypropoxy}quinoline trihydrochloride (XII) essentially as shown below for the free base of the anti isomer (IVa)in step 6.

Examples 2–27

A representative sample of experimental results obtained for the selective crystallization of syn and anti isomer compounds of formula III and IVa respectively is shown in table 1 below:

TABLE 1

| Acid Used | Solvent | Starting ratio (anti/syn) | Final ratio (anti/syn) | Yield (anti) |
|---|---|---|---|---|
| HBr | $CH_2Cl_2$ | 99.3/0.7 | 99.8/0.2 | 96.9% |
| MsOH | $CH_2Cl_2$ | 87/13 | no precip. | 0% |
| HBr | EtOAc | 55/45 | 65/35 | 72.6% |
| HBr | EtOAc | 84/16 | 98.1/1.9 | 63.3% |
| HCl | EtOAc | 85/15 | 89.4/10.6 | 87.0% |
| (−)-CSA* | EtOAc | 85/15 | 98.9/1.1 | 69.3% |
| (+)-CSA | EtOAc | 87/13 | 98.5/1.5 | 25.8% |
| MSOH | EtOAc | 87/13 | 87.0/13.0 | 46.4% |
| p-TSOH* | EtOAc | 87/13 | 98.5/1.5 | 23.7% |
| $H_2SO_4$ | EtOAc | 85/15 | no precip. | 0% |
| (+)-CSA | EtOH | 78/22 | 98.8/1.2 | 66.6% |
| MsOH | EtOH | 78/22 | 8.0/92.0 | 48.5%** |
| p-TsOH | EtOH | 78/22 | no precip. | 0% |
| (+)-CSA | EtOH | 85/15 | 98.7/1.3 | 72.6% |
| MSOH | EtOH | 85/15 | 9.7/90.3 | 69.8%** |
| $H_2SO_4$ | EtOH | 85/15 | 91.0/9.0 | 64.4% |
| HBr (2 eq) | EtOH | 85/15 | 80.0/20.0 | 56.6% |
| HCl (2 eq) | EtOH | 85/15 | 98.9/1.1 | 56.1% |
| MsOH | EtOH | 17/83 | 2.9/97.1 | 96.7%** |
| (−)-CSA | EtOH | 85/15 | 98.6/1.4 | 66.4% |
| (+)-CSA | EtOH | 64/36 | 98.9/1.1 | 21.7% |
| (+)-CSA | EtOH | 87/13 | 99.3/0.7 | 65.8% |
| $HClO_4$ | $Et_2O$ | (2 eq) | 86.7/13.3 | 91.5% |
| $HClO_4$ | $Et_2O$ | 85/15 | no precip. | 0% |
| p-TsOH | $CH_2Cl_2$ | 87/13 | no precip. | 0% |
| $HBF_4$ | $Et_2O$ | 85/15 | no precip. | 0% |

*CSA is camphorsulfonic acid and p-TSOH is p-toluenesulfonic acid.
**Yield of syn-isomer salt recovered from the mixture. Methanesulfonic acid (mesylate) salts exhibited a reversal of solubilities in EtOH so that the syn mesylate salt was less soluble.

Although the use of the syn isomer (1aα,6β,10bα)-1,1-difluoro-1,1a,6,10b-tetrahydrodibenzo[a,e]cyclopropa[c]cyclohepten-6-ol compound of formula (ii) and the anti isomer (1aα,6α,10bα)-6-halo-1,1-difluoro-1,1a,6,10b-tetrahydrodibenzo[a,e]cyclopropa[c]cycloheptene (iii) have been described and exemplified above, this invention is not intended to be limited by the disclosure herein. One skilled in the art is aware that formation of the (1aα,6α,10bα)-1-(1,1-difluoro-1,1a,6,10b-tetrahydrodibenzo[a,e]cyclopropa-[c]cyclohepten-6-yl)-piperazine compound (II) is possible with either the syn isomer (1aα,6α,10bα)-6-halo-1,1-difluoro-1,1a,6,10b-tetrahydrodibenzo[a,e]-cyclopropa[c]cycloheptene or the trans isomer (1aα,6α,10bα)-6-halo-1,1-difluoro-1,1a,6,10b-tetrahydrodibenzo[a,e]cyclopropa[c]cycloheptene compound of formula (iii). This is made possible by the difluoromethanodibenzosuberane tropylium ion intermediate for the formation of a compound of formula (II) from the compound of formula (iii).

Likewise, one skilled in the art is aware that the use of the syn difluoromethanodibenzosuberol compound of formula (ii) is not critical to the practice of this invention. The corresponding anti difluoromethanodibenzosuberol compound would be equally effective. This is because the formation of the anti isomer (1aα,6α,10bα)-6-halo-1,1-difluoro-1,1a,6,10b-tetrahydrodibenzo[a,e]cyclopropa[c]cycloheptene (iii) and the syn isomer (1aα,6β,10bα)-6-halo-1,1-difluoro-1,1a,6,10b-tetrahydrodibenzo[a,e]cyclopropa[c]-cycloheptene proceed via the corresponding tropylium ion intermediate which in the case of the bromide provides the anti isomer compound of formula (iii) preferentially, by the method of this invention.

We claim:
1. A compound of the formula (IVa):

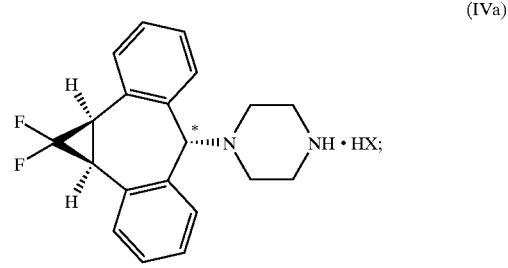

(IVa)

wherein HX is an acid selected from the group consisting of hydrogen chloride, hydrogen bromide, camphorsulfonic acid, and sulfuric acid.

2. A compound of the formula (IIIa):

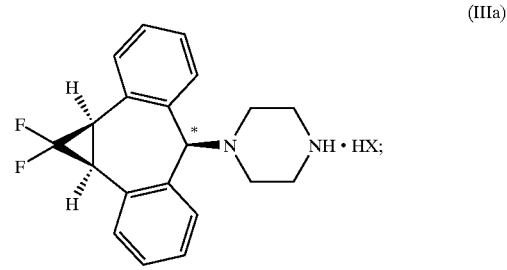

(IIIa)

wherein HX is an acid selected from the group consisting of hydrogen chloride, hydrogen bromide, and camphorsulfonic acid.

3. A process for preparing a compound of the formula (IVa):

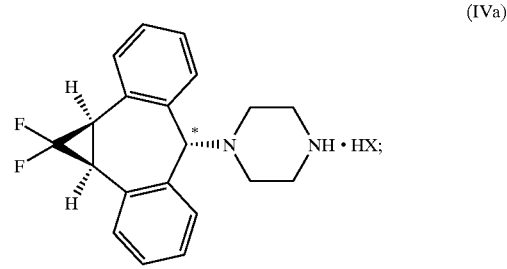

(IVa)

wherein HX is an acid, selected from the group consisting of hydrogen chloride, hydrogen bromide, (−)-camphorsulfonic acid, and (+)-camphorsulfonic acid, comprising the steps of:

(a) dissolving a compound of formula (II)

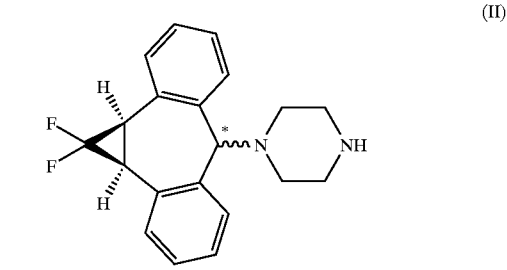

(II)

in acetonitrile to form a solution;

(b) crystallizing a syn stereoisomer compound of formula (III)

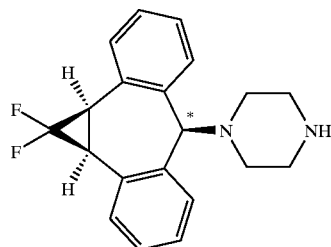

from the solution of (II);

(c) removing the acetonitrile from the filtrate to provide a mixture enriched in an anti stereoisomer compound of formula (IV)

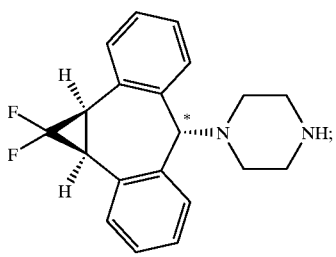

(d) adding an acid and solvent selected from the group consisting of hydrogen chloride and ethyl acetate, hydrogen bromide and methylene chloride, hydrogen bromide and ethyl acetate, (−)-camphorsulfonic acid and ethyl acetate, and (+)-camphorsulfonic acid and ethanol; and (e) crystallizing the anti-stereoisomer compound of formula (IVa).

4. The process according to claim 3 wherein the acid is hydrogen bromide.

5. The process according to claim 3 further comprising the step of:

(a) reacting the anti-stereoisomer (IVa) as the free base, with (R)-1-(5-quinolinyloxy)-2,3-epoxypropane to provide compound of formula (V);

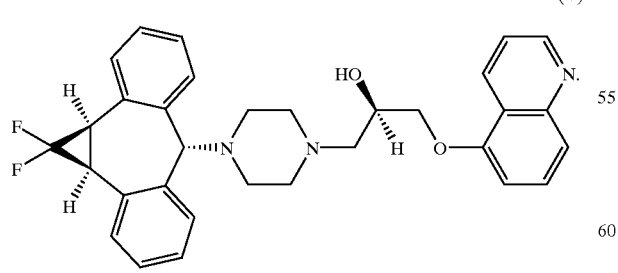

6. The process according to claim 5 further comprising the step of:

(a) reacting hydrogen chloride with compound (V) to form a compound of formula (I):

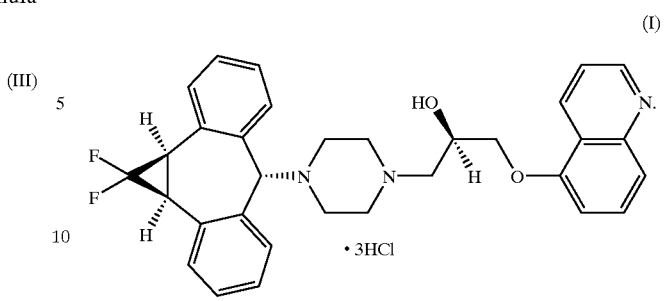

7. A process for preparing a compound of the formula (IIIa):

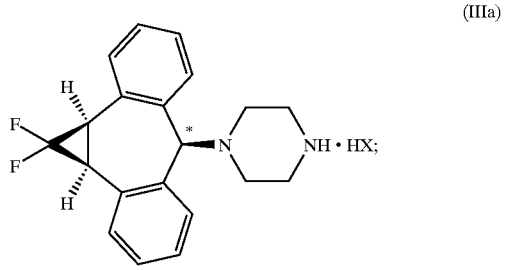

wherein HX is an acid, selected from the group consisting of hydrogen chloride, hydrogen bromide, (−)-camphorsulfonic acid, and (+)-camphorsulfonic acid, comprising the steps of:

(a) dissolving the compound of formula (II)

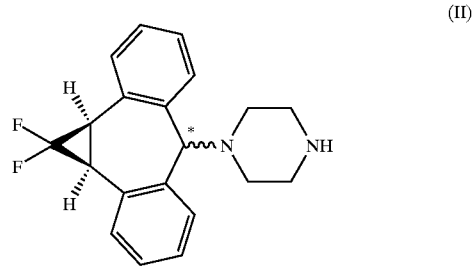

in acetonitrile to form a solution;

(b) crystallizing the syn stereoisomer (III)

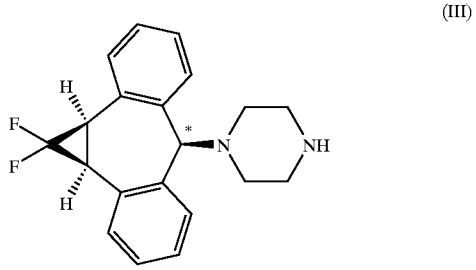

(c) adding an acid and solvent selected from the group consisting of hydrogen chloride and ethyl acetate, hydrogen bromide and methylene chloride, hydrogen bromide and ethyl acetate, (−)-camphorsulfonic acid and ethyl acetate, and (+)-camphorsulfonic acid and ethanol; to the syn stereoisomer (III); and (d) crystallizing the syn-stereoisomer compound of formula (IIIa).
8. The process according to claim 7 further comprising the steps of:
(a) reacting the syn-stereoisomer (III) with (R)-1-(5-quinolinyloxy)-2,3-epoxypropane to provide the syn isomer compound (XI);
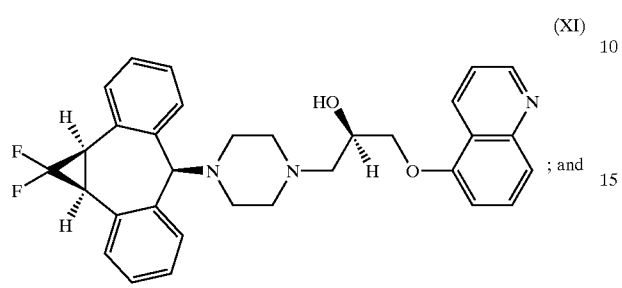
(XI)
; and
(b) optionally reacting hydrogen chloride with compound (XI) to form a compound of formula (XII):
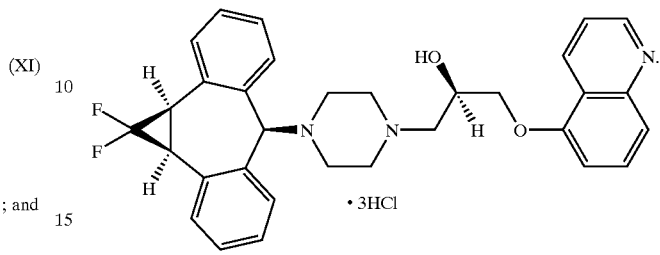
(XII)
• 3HCl
* * * * *